United States Patent [19]

Thirumalachar et al.

[11] Patent Number: 4,673,687

[45] Date of Patent: Jun. 16, 1987

[54] NEW CHEMOTHERAPEUTIC AGENTS FOR THE CONTROL OF PLANT AND ANIMAL DISEASES

[75] Inventors: Mandayam J. Thirumalachar; Mandayam J. Narasimhan; Mandayam J. K. Thirumalachar, all of Bangalore, India

[73] Assignee: Source Technology Biologicals, Inc., Minneapolis, Minn.

[21] Appl. No.: 758,322

[22] Filed: Sep. 5, 1985

Related U.S. Application Data

[62] Division of Ser. No. 487,842, Apr. 22, 1983, Pat. No. 4,544,666.

[51] Int. Cl.$^4$ .......................... C07C 1/08; H01N 37/10
[52] U.S. Cl. .................................. 514/460; 514/499; 556/110; 556/116
[58] Field of Search .............. 260/429 J, 438.1, 501.13; 556/110, 116; 514/499, 460

[56] References Cited

U.S. PATENT DOCUMENTS

| | | | |
|---|---|---|---|
| 2,950,309 | 8/1960 | Cavallito | 560/68 |
| 4,359,430 | 11/1982 | Heikkilä et al. | 260/501.13 |
| 4,421,927 | 12/1983 | Picart | 260/501.13 |

Primary Examiner—Glennon H. Hollrah
Assistant Examiner—Raymond Covington
Attorney, Agent, or Firm—Burd, Bartz & Gutenkauf

[57] ABSTRACT

A chemotherapeutic composition for the control of plant diseases caused by mycoplasma-like organisms, rickettsia-like organisms, or seed-borne legume viruses. The composition is composed essentially of the tannate complex of picro ammonium formate combined with a minor amount of a surfactant sufficient to prevent formation of ammonium picrate. The preparation and use of the composition are disclosed. Also disclosed is a related chemotherapeutic composition for the control of plant diseases caused by plant pathogenic fungi and bacteria and composed essentially of a tannate complex of picro cupric ammonium formate in aqueous solution combined with a minor amount of a surfactant sufficient to prevent formation of ammonium picrate, along with its method of preparation and manner of use.

8 Claims, No Drawings

NEW CHEMOTHERAPEUTIC AGENTS FOR THE CONTROL OF PLANT AND ANIMAL DISEASES

This is a division of application Ser. No. 487,842 filed Apr. 22, 1983 now U.S. Pat. No. 4,544,666.

FIELD OF THE INVENTION

This invention relates broadly to the field of chemotherapeutic control of plant and animal diseases caused by certain organisms.

BACKGROUND OF THE INVENTION

One aspect of this invention relates to the chemotherapeutic control of plant diseases caused by a group of organisms termed mycoplasma-like organisms (MLO) and rickettsia-like organisms (RLO) with a novel chemotherapeutic agent designated KT-198. KT-198 is a tannate complex of picro ammonium formate combined with a minor amount of a surfactant sufficient to prevent formation of ammonium picrates. Both MLO and RLO were previously thought to be viruses since they pass through filters that hold back bacteria and could not be detected by ordinary light microscope. With the development of electron microscopy and new microbiological techniques, these have been shown to be organisms which could be cultivated on special nutrient media, and at least for some of them Koch's postulates have been established. The RLO are walled organisms and inhabit xylem or phloem cells depending on the species concerned. Some of the serious diseases of plants such as phony peach, Pierce's diseases of grapes, citrus greening and die-back, grassy shoot of sugar cane, etc. are examples of RLO diseases.

More than 50 diseases of plants at one time considered to be of viral origin have now been shown to be mycoplasmas (including the motile Spiroplasma). Very important plant diseases such as elm phloem necrosis, yellow lethal wilt of coconut, sandal spike disease, X-disease of peach, pear decline, potato witches broom, corn stunt, yellow dwarf of rice, aster yellows, mulberry dwarf, etc. have been shown to be of MLO origin. More and more examples are being found. Another group of diseases for which the chemotherapeutant of the present invention, KT-198, has been developed is against some of the legume viruses which are seed-borne.

Another aspect of this invention relates to the chemotherapeutic control of plant diseases where the causal organisms are plant pathogenic fungi and bacteria with another novel chemotherapeutic agent of this invention designated KT-19827. KT-19827 is a tannate complex of picro cupric ammonium formate in aqueous solution combined with a minor amount of a surfactant sufficient to prevent formation of ammonium picrate.

This new chemotherapeutic agent is useful in the control of the following types of diseases and similar plant diseases:

(1) Internally and externally seed-borne fungal and bacterial diseases of plants.

(2) Downy mildew and powdery mildews of plants caused by fungi.

(3) Root rots and wilt diseases of plants where the organisms are soil-borne, and where many of the conventional fungicides cannot be used since they affect the living root system.

(4) Systemically infected trees where the fungus is in the vascular tissues and only those systemic fungicides which when injected are translocated inside the vascular strands can be used. As examples, the oak wilt disease and the Dutch elm disease, both caused by different species of the fungus Ceratocystis. These diseases have remained "incurable" up to the present time. The present novel fungicide is the first of its kind which has proved effective in more than 900 treated trees, effectively controlling the disease.

(5) A large number of plant bacterial diseases incited by species of the genus Xanthomonas, Pseudomonas, Erwinia and Corynebacterium, which up to the present were controlled chiefly by the use of antibiotics such as streptomycin and tetracyclines or their combination. Due to the development of antibiotic resistant bacterial strains, such diseases have no direct control measures now. No really effective bactericide is yet available though partial effect has been claimed with many compounds. The novel bactericide of this invention offers the first effective control of phytopathogenic bacterial pathogens, both as seed treatment, plant dips and spray schedules.

THE PRIOR ART

In both RLO and MLO diseases, the only means of control has been treating the plants by injections or spray schedules with tetracyclines. These bring about temporary regression of the symptoms, which, however, reappear after some time.

There are very few antiviral chemotherapeutants known for control of animal viruses, and much less for plant viruses. Among a few of the clinically used chemotherapeutants against DNA animal viruses, mention may be made of idoxuredine, arabinofuranosylcytosine, arabino-furanosyladenine, methisazone and 6-azauredine. Some of the chemotherapeutants against oncogenic viruses include cyclohexamide, noformacin, ribavirin, dimethylbenzylrifampicin, etc.

Of particular interest in the developement of antiviral substances which has direct bearing on the present chemotherapeutant, KT-198, is the most recent discovery of trisodium phosphoformate as an effective antiviral agent in vivo against cutaneous herpes-virus infection in guinea pigs (Stefan Alenius, Zvonimir Dinter, and Bo Oberg, in Antimicrobial Agents and Chemotherapy, September 1978, 408-413). It may be pointed out that none of the above known chemotherapeutic agents are active against plant viruses and none are known to be controlling of mycoplasma-like organisms or rickettsia-like organisms causing plant diseases.

Among compounds used as fungicides, bactericides and anti-fouling agents (including killing of algae), copper compounds are well known and numerous patents have been granted for their use. These copper compounds can be grouped under two headings:

(1) WATER SOLUBLE COPPER COMPOUNDS—All soluble copper compounds are highly toxic to the living plants and are used only on dead materials such as cellulose fibers, as components of wood preservatives, anti-fouling agents where the intention is killing the polluting agent, like algae in ponds, etc. When used on living plant tissue, they show high phyto-toxicity, burn and kill the plants. The soluble copper compounds previously used include (a) cupric sulphate, (b) cupric acetate, (c) cupric chloride and cupric chlorate, (d) cupric formate, also called Tubercuprose, (e) cupric hexafluorosilicate, (f) cupric nitrate, (g) cupric chromate (used in preventing growth of fungi and bacteria infesting cellulose fibers), and (h) cupric ammonium complex.

(2) WATER INSOLUBLE COPPER COMPOUNDS—All copper fungicides used at present are water insoluble complexes, and form deposits on the treated parts as colloidal layers. When the fungus spore germinates on the surface, soluble copper is released and the fungus is killed. In brief, none of the presently existing fungicides is absorbed and translocated within the plant tissue without killing the host cells as well as killing the fungal or bacterial pathogen.

SUMMARY OF THE INVENTION

Broadly stated, the chemotherapeutic agent designated KT-198, is a tannate complex of picro ammonium formate combined with a minor amount of a surfactant sufficient to prevent formation of ammonium picrate. The picro ammonium formate is produced without the concurrent production of ammonium picrate by reacting picric acid (2,4,6 trinitrophenol) with ammonium formate in a viscid solution of ammonium formate containing a surfactant, such as an alkali metal alkyl sulphate in amount sufficient to prevent formation of ammonium picrate, and combining with tannic acid. For each 100 parts by dry weight of ammonium formate in the complex, picric acid is present in amount between about 2 to 5 parts by weight, tannic acid is present in amount between about 0.5 to 2 parts by weight, and the surfactant is present in amount between about 2 to 10 parts by weight.

Broadly stated, the fungicide and bactericide designated KT-19827 is a tannate complex of picro cupric ammonium formate in aqueous solution combined with a minor amount of a surfactant sufficient to prevent separation of ammonium picrate. The complex is produced by reacting cupric sulphate with ammonium formate, combining with tannic acid and complexing with picric acid, in aqueous solution containing a minor amount of a surfactant sufficient to prevent separating out of the tannate complex. One mole of a water soluble cupric salt, such as cupric sulphate, is reacted with a stoichiometric equivalent of 2 moles of ammonium formate, or with a stoichiometric excess of 15 to 45 percent by weight of ammonium formate (2.3 to 2.9 moles) and this product is complexed with picric acid. For each 100 parts by dry weight of cupric ammonium formate, picric acid is added in amount between about 2 and 5 parts by weight, surfactant is added in amount between about 2 to 10 parts by weight and tannic acid is added in amount between about 0.5 to 3.5 parts by weight.

DETAILED DESCRIPTION OF THE PREFERRED EMBODIMENT

A. PRODUCTION OF KT-198

The present chemotherapeutant, KT-198, is a tannate complex of picro ammonium formate combined with a minor amount of a surfactant sufficient to prevent formation of ammonium picrate. KT-198 is a highly water soluble stable compound and relatively non-toxic to animals and plants at doses used to control the diseases under consideration.

According to the present invention, in the process for the production of KT-198, ammonium formate is dissolved in water to which known amounts of a surfactant and tannic acid are added. The mixture is warmed on a water bath at 60° C. and this results in formation of a viscid solution. When solid picric acid in known quantity is added, it goes into solution after considerable lapse of time, depending upon the quantity handled and physical conditions, such as agitation, etc. There is no formation of precipitate of ammonium picrate as in the case of direct addition of picric acid to an ammonium formate solution. All the picric acid goes into solution with the formation of picro ammonium formate, and, with sodium lauryl sulphate as the surfactant and tannic acid, there is produced the tannate complex of picro ammonium formate. The KT-198 is a dark brownish-yellow material which is very stable, and completely soluble in water to produce a golden-yellow solution.

With this as the background, the following details for the preparation of KT-198 are described below:

EXAMPLE A-1

The following details of preparation are followed for producing about one kilogram of KT-198: 800 grams of ammonium formate are added to 400 cc of water; 80 grams of sodium lauryl sulphate and 40 grams of tannic acid are added to the solution and warmed on water bath at 60° C. for 30 minutes. The mixture is well agitated, and cooled to room temperature (24° C.) and 40 grams of picric acid are added and well shaken. The picric acid settles down mostly at the bottom, and as it slowly dissolves over a period of 6 to 24 hours, the entire mass turns uniformly brownish-yellow. The mixture is kept at 50° to 60° C. which makes the reaction complete and also evaporates the water. Water may be further evaporated in a vacuum oven at 35° to 40° C. The resulting dry powder may be stored as such or formulated for use in plant disease control.

EXAMPLE A-2

According to an alternate method of preparing KT-198, 40 grams of sodium lauryl sulphate and 20 grams of tannic acid are dissolved in 200 cc of water containing 400 grams of ammonium formate prior to the addition of 20 grams of picric acid in 500 cc propylene glycol, all at room temperature. The tannate complex of picric ammonium formate is produced and there is no dissociation and separating out of ammonium picrate, whose solubility in water is low (1 gram in 100 cc of $H_2O$ at 20° C.) and readily separates out. The role of sodium lauryl sulphate addition to ammonium formate prior to reaction with picric acid, is to prevent formation of ammonium picrate.

B. PRODUCTION OF KT-19827

The chemotherapeutic, KT-19827, is a tannate complex of picro cupric ammonium formate in aqueous solution combined with a minor amount of a surfactant sufficient to prevent separating out of the tannate complex. KT-19827 is a soluble complex and is also relatively non-toxic to animals and plants at doses used to control bacterial and fungal plant diseases, and viral and mycoplasma diseases also previously mentioned as controlled by KT-198.

Cupric ammonium formate $CuNH_4(HCOO)_2$ is produced when one mole of cupric sulphate is reacted with 2 moles of ammonium formate in aqueous medium. Tannic acid addition to this results in formation of the tannate complex, which is water soluble gradually dissociating into water insoluble cupric tannate. It has been pointed out by studies of A. W. Davidson and Vernon Holm (Journal of American Chemical Society 53:1350–1357, 1931) that the solubility of cupric ammonium formate increases with excess addition of ammonium formate up to 43.75 mole percent. There is no solid phase separating out, and on slight warming a deep violet bluish solution is formed. A ternary system $NH_4CHO_2$—$Cu(CHO_2)_2$—$HCHO_2$ is formed. While this resembles cupric ammoniate solution formed by addition of excess of ammonia to cupric sulphate solution, the presence of the formate in the complex makes it totally different.

The avidity of picric acid to form complexes with copper ammoniates is well known. Joshi and Bhargava (Journal of Indian Chemical Society 40: 19–22, 1963; Chemical Abstracts, 58: 13408 d, 1963) showed that when picric acid is added to a cupric ammoniacal solution, an olive green precipitate is formed which by spectrophotometric study showed that the picric acid copper ammoniate complex had one part of $Cu(NH_3)_4++$ and 2 parts of picric acid. N. P. Agafoshin (Chemical Abstracts 32: 72, 1938) reported that complex compounds of picric acid with copper ammoniates are formed when aqueous solutions of picric acid are added to $NH_4OH$ solution of $Cu(OH)_2$. A precipitate of the complex is formed with the formula $[(C_6H_2(NO_2)_2O)]_2$-$(CuNH_2)_4$.

A similar complex is formed when picric acid is reacted with cupric ammonium formate solution. However, unlike cupric ammoniate solution, there is no formation of precipitate, but a soluble complex.

The physical properties of the product also show the formation of the new complex, KT-19827. Cupric sulphate has no melting point but decomposes at 560° C. and above. Ammonium formate has a melting point of 116° C. When cupric ammonium formate complex is produced and evaporated to dryness, a hard bluish material is formed, which will not melt even when autoclaved at 120° C. After the formation of the picrate complex of cupric ammonium formate, the product melts at 60° C. and can be handled as a thick viscid liquid. Hence, the KT-19827 fungicide-bactericide can be constituted in any formulation. A water-soluble tannate complex of picro-cupric ammonium formate is formed. The product is a greenish-brown to olive-green material which on dissolving in water forms a pale yellowish-brown solution with fungicidal and bactericidal properties.

The details for the production of KT-19827 are described below:

EXAMPLE B-1

20 grams of tannic acid is dissolved in 200 ccs of water to which 400 grams of pure (technical grade) ammonium formate is added and the solution is warmed up to 70° C. 400 grams of copper sulphate, pentahydrate, is powdered and added and mixed thoroughly. 40 grams of sodium lauryl sulphate is added and thoroughly mixed. 20 grams of picric acid is added, thoroughly mixed and dried in a vacuum oven at 40° C. A pasty greenish-black water soluble mass is produced which can be stored at room temperature for long periods. 250 grams of the KT-19827 thus produced is weighed and titurated with 500 ccs of commercial non-phosphate dishwashing detergent or propylene glycol. The whole mixture forms a viscid mass, which can be disposed to containers in measured quantities for dilution and use in the field.

EXAMPLE B-2

800 grams of ammonium formate is added to 400 ccs of water. 80 grams of sodium lauryl sulphate and 40 grams of tannic acid are added and warmed on water bath at 60° C. for 30 minutes. The mixture is well agitated, and cooled to room temperature (24° C.). 800 grams of powdered cupric sulphate is added, and 40 grams of picric acid dissolved in 500 cc of propylene glycol is added and well shaken. The picric acid settles down mostly at the bottom, and as it slowly dissolves over a period of 6 to 24 hours, the entire mass turns uniformly brownish-yellow.

That stiochiometrically equivalent amounts of ammonium formate to cupric sulphate may be used is illustrated by the following:

EXAMPLE B-3

126 grams of ammonium formate (M.W. 63) is dissolved in 200 ccs of water containing 10 grams of tannic acid. 159 grams of cupric sulphate (anhydrous) (M.W. 159.6) is added, and warmed on a water bath at 60° C. unitl a clear deep blue solution is formed. 20 grams of sodium lauryl sulphate is now added and the mixture agitated until all the sodium lauryl sulphate dissolves. A deep greenish-blue solution is formed. 10 grams of picric acid is dissolved in 500 ml of commercial non-phosphate dishwashing detergent or propylene glycol. The picric acid dissolves slowly and forms a complete solution with no precipitate. This solution is added slowly to the solution above and mixed well.

EXAMPLE B-4

20 grams of tannic acid is dissolved in 200 ccs of water. 252 grams of ammonium formate are added and dissolved. 40 grams of sodium lauryl sulphate is added, and the solution containing tannic acid, ammonium formate and sodium lauryl sulphate is warmed on a water bath 60° C. for 15 minutes. 318 grams of anhydrous cupric sulphate is added and agitated until a homogenous thick solution is formed. 250 ccs of commercial non-phosphate dishwashing detergent or propylene glycol, is added to the above, and this makes the cupric ammonium formate double salt complex of tannic acid with sodium lauryl sulphate, as a homogenous product. 20 grams of picric acid is added to 500 ccs of commercial non-phosphate dishwashing detergent or propylene glycol, and allowed to stand until all picric acid goes into solution. This solution is added to the solution above and mixed well. A partly water soluble tannate complex of picro cupric ammonium formate is formed.

The presence of a surfactant in KT-198 and KT-19827 serves several purposes. The surfactant acts as a spreader when the chemotherapeutic agent is sprayed. It also enhances the diffusion of the agent into remote pockets within the plant when plant injections with the agent are made. Other surfactants may be used in KT-19827, such as other alkali metal alkyl sulphates.

The role of picric acid is as a mordant on the walls of the pathogens which then in the case of KT-19827 permits greater penetration. Penetration of the copper complex through the pathogen walls and the plant cell walls is enhanced by it being complexed with the ammonium formate into a more soluble ionizable form.

The effect of tannic acid addition in KT-19827 is antidoting phytotoxicity of copper.

C. CHEMOTHERAPEUTIC USE OF KT-198

The following examples illustrate the use of KT-198 in controlling plant and animal diseases. For example, the chemotherapeutant KT-198 may be formulated in glycerine only, or a mixture of glycerine and a water miscible solvent like methyl cellosolve mixed in equal quantities on volume bases. In control of plant diseases, KT-198 may be formulated in any agriculturally acceptable, non-toxic carrier.

EXAMPLE C-1

Elm phloem necrosis is a serious wilt disease of elms in the United States caused by a mycoplasma-like organism. The progress of the disease symptoms extends over several years, from yellowing die-back of shoots to final wilting.

Experiments were carried out to determine the effectiveness of KT-198 in controlling the elm phloem necrosis. Five grams of KT-198 dissolved in a gallon of water (about 0.13%) was pressure injected into the trunks of ten trees during the months of August–September, using the Reil pressure injection apparatus. Four untreated trees served as controls and eight trees treated with Terramycin, a tetracycline, served as a comparison of a prior art treatment. In October of the next year, results showed that KT-198 was superior to tetracycline. 75 percent of the untreated trees died. 69 percent of tetracycline treated trees died. None of KT-198 treated trees died.

cent or green flowers. 10 Vinca rosea cuttings with severe infection of aster yellows were steeped in a 550 ppm solution of KT-198 (about 0.055%) for three hours and then planted: ten other cuttings, serving as controls, were steeped in water only and then planted. As positive control, 10 diseased cuttings were steeped for three hours in 1000 ppm of oxytetracycline hydrochloride. Tetracyclines (Chlor, Oxy and tetracycline hydrochlorides) are the only chemotherapeutants known for controlling mycoplasma-like diseases (MLO). After a period of 45 days, all the cuttings had rooted. The controls showed 100 percent infection. KT-198 treated cuttings showed no disease symptoms, and were normal and healthy. Seven of the oxytetracycline-treated cuttings survived, and they were free from symptoms, but showed severe etiolation due to phytotoxicity of oxytetracycline.

EXAMPLE C-3

Citrus greening and die-back is a severe disease of citrus caused by rickettsia-like organism in the phloem. It is a limiting factor in citrus production in Asia, South America and Australia, though absent in the United States, where a close relative of this rickettsia causes

| Specimen No. | Symptom at time of Injection | | Size of Elm (diameter in inches at breast height) | Date initially injected | Total amt, injected in gms. (no. in parenthesis is no. of times injected) | Chemotherapeutic | Condition of Elm tree in Oct. of following year |
|---|---|---|---|---|---|---|---|
| | % Necrotic clinging leaves | Percent defoliation | | | | | |
| 1 | 35 | 20 | 38 | June 6 | 16.8 (1) | Terramycin 70% | Dead |
| 2 | 4 | 1 | 28.0 | June 9 | 51.8 (7) | Terramycin 70% | Dead |
| 3 | 0 | 1 | 33.0 | June 14 | 61.0 (8) | Terramycin 70% | Dead |
| 4 | 10 | 1 | 34.0 | June 14 | 53.2 (7) | Terramycin 70% | Dead |
| 5 | 0 | 0 | 20.0 | June 18 | 4.2 (1) | Terramycin 70% | Dead |
| E-2 | 0 | 0 | 5.0 | Control | Control | Control | Dead |
| E-4 | 0 | 0 | 9.0 | Control | Control | Control | Healthy |
| CE-1 | 5 | 0 | 36.2 | Aug. 13 | 5.0 (1) | KT-198 | Healthy |
| CE-2 | 5 | 0 | 26.0 | Aug. 13 | 5.0 (1) | KT-198 | Healthy |
| CE-4 | 10 | 0 | 20.6 | Aug. 13 | 5.0 (1) | KT-198 | Healthy |
| CE-5 | 10 | 0 | 39.1 | Aug. 13 | 5.0 (1) | KT-198 | Healthy |
| CE-7 | 10 | 0 | 24.4 | Aug. 13 | 5.0 (1) | KT-198 | Healthy |
| CE-10 | 5 | 0 | 29.8 | Sept. 3 | 5.0 (1) | KT-198 | Some decline at top |
| CE-12 | 5 | 0 | 27.0 | Sept. 3 | 5.0 (1) | Terramycin 70% | Healthy |
| CE-14 | 5 | 0 | 32.0 | Control | Control | Control | Dead |
| CE-15 | 5 | 0 | 41.0 | Sept. 3 | 10.0 (1) | KT-198 | Healthy |
| CE-16 | 5 | 0 | 17.0 | Control | Control | Control | Dead |
| CE-18 | 3 | 0 | 29.7 | Sept. 3 | 5.0 (1) | Terramycin 70% | Considerable decline |
| CE-19 | 1 | 0 | 31.0 | Sept. 3 | 5.0 (1) | KT-198 | Marginal |
| CE-21 | 5 | 0 | 21.7 | Sept. 6 | 5.0 (1) | KT-198 | Healthy |
| CE-24 | 2 | 0 | 24.9 | Sept. 6 | 5.0 (1) | KT-198 | Healthy |
| CE-25 | 5 | 0 | 21.0 | Sept. 6 | 10.0 (1) | Terramycin 70% | Healthy |
| CE-22 | 20 | 5 | 37.2 | Sept. 6 | 5.0 (1) | Terramycin 70% | Dead |

| Treatment | Total Number of Trees | Summary Number Healthy | Number Marginal | Number Dead |
|---|---|---|---|---|
| KT-198 | 10 | 8 (80%) | 2 (20%) | 0 (0%) |
| Terramycin 70% | 9 | 2 (22%) | 1 (11%) | 6 (67%) |
| Control | 4 | 1 (25%) | 0 (0%) | 3 (75%) |

EXAMPLE C-2

The disease caused by aster yellows on Vinca results in formation of witches broom-like growth, with viresyoung tree decline of citrus in Florida. The only known treatment so far is injecting tetracycline compounds such as chlortetracycline, oxytetracycline and tetracycline into the stem. The diseased trees recover, but after several months the disease reappears because the tetracyclines only have static effect and not cidal effect.

The disease symptoms of citrus greening and die-back are very conspicuous, by the yellowing and drying up of the shoots from the top. Such plants can be easily diagnosed. 100 diseased trees were selected and divided into four groups of 25 plants each. The treatments were:

(1) KT-198: One gram per tree of KT-198 dissolved in 500 ccs of water (about 0.2%) and injected into the trunk of the tree. Injection was carried out from a feed bottle serving as tank for the chemical solution and infused into the stem through a plastic tube into a hole bored in the stem. In 4 to 8 hours all the solution is taken up by the plant.

(2) Oxytetracycline hydrochloride: 500 ppm in 500 ccs of water.

(3) Tetracycline hydrochloride: 500 ppm solution in 500 ccs of water.

(4) Controls with water only.

The remission of disease symptoms is indicated by the development of new flush green leaves filling up the gap between wilting shoots and by the tree beginning to bear flowers and fruits. This is seen three months after treatment with KT-198. In controls, all the trees remained diseased, some of them showing more advanced symptoms. All the KT-198 treated trees showed recovery depending upon the severity of the disease before treatment. Tetracyclines were effective in reducing the symptoms, but the plants showed yellowing due to phytotoxicity of tetracyclines. At the end of two years, all the KT-198 treated plants remained healthy. Eight of the oxytetracycline treated, and four of the tetracycline treated trees, showed greening and die-back symptoms again.

The above two examples illustrate effective control of both MLO and RLO diseases, by KT-198 treatment. Several other MLO and RLO diseases have similarly been treated and controlled.

EXAMPLE C-4

Among the plant viruses, soybean yellow mosaic is taken as an example for legume virus controlled by KT-198. Diseased seeds, which can be identified by the brown patch near the hilum, are treated with the glycerine formulation containing 2.5 grams KT-198 in 10 cc (about 25%). The seeds are kept for 12 hours after treatment at room temperature during which time the chemotherapeutant is absorbed within. The treated and untreated seeds (serving as controls) are planted and observed for disease symptoms. The yellow mosaic disease of soybean can be discerned when the second leaf stage comes up, the diseased plants showing mosaic and crinkling symptoms. Ninety-five percent of the treated seeds become disease free, while all the controls show disease symptoms. With a spray schedule of KT-198 (10 cc in a liter of water which would contain 500 ppm of active ingredient), the disease in the afflicted five percent of the plants is well controlled.

D. CHEMOTHERAPEUTIC USE OF KT-19827

The following examples illustrate the use of KT-19827 in controlling fungal and bacterial plant diseases. KT-19827 fungicide-bactericide may be formulated in several ways, as in an agriculturally acceptable non-toxic solvent, and one of the preferred methods is formulating it in commercial glycerine. One part by weight of the KT-19827 is mixed with two parts by volume of glycerine (about 50%). It forms a homogeneous formulation and has long shelf life.

The following examples illustrate the plant protection activities of KT-19827:

EXAMPLE D-1

Dutch elm disease incited by *Ceratocytis ulmi* is a devastating disease which has not been effectively controlled so far. The disease is vascular, and is transmitted by the elm beetle which carries the spore load from tree to tree in its breeding cycle. Few expensive chemicals such as Lignasan (MBC-hydrochloride) of the Benomyl group, and Arbotect, have only static effect and temporarily halt the disease, but there is no regression of symptoms.

In Minnesota, diseased elm trees in the advanced stage of the disease were pressure injected with the KT-19827 solution (50 ml of KT-19827 formulation in 10 liters of water, i.e., 0.5%). Whereas in very severely diseased trees the progression of the disease was arrested, in the moderate and moderate to severely diseased, the symptoms begin to regress in three weeks (21 days) with the appearance of new healthy leaves which were green and full of vigor.

In other parts of the United States, more than 900 trees have been treated with a high percentage of protection and even control of the disease. For a large-sized tree with a stem girth of 60 to 70 inches, six to eight holes are bored along the circumference of the tree at shoulder height. Nipples are inserted, which are all connected together by a plastic tube onto a pressure vessel in which 12 to 15 liters of a 500 ppm solution of KT-19827 (0.05%) is placed. At 25 psi, the KT-19827 solution is carried into the tree at the injection points, and within 4 to 24 hours (depending upon the weather conditions affecting transpiration and water-flow within the tree), there is complete uptake of the fungicide solution. The already infected branches are pruned off, and an insecticidal spray is given to ward off elm beetles. Observations have been recorded over a period of several years, and results showed that where there previously was an annual Dutch elm wilting of 10 to 15 percent of trees with or without the use of other chemicals for control, KT-19827 reduced tree losses to less than two percent. After treatment with KT-19827, some of the trees marked for cutting down evidenced control of the disease and resumed normal appearance and growth.

KT-19827 thus demonstrates a totally unexpected ability to quickly translocate from the original injection situs through the entire tree, from roots to crown leaves. This translocating ability of KT-19827 eliminates the necessity of having to girdle the tree at the ground line in order to bring the chemotherapeutic within the root system.

EXAMPLE D-2

*Citrus gummosis,* a devastating disease, caused by two Phytophtora species, *P. palmivora* and *P. citrophthora,* was controlled by treating the diseased trees with 10 gallons of KT-19827 solution (1 percent of the formulation in detergent), and the trunk and limbs with heavy gummosis were swabbed with a 5 percent solution of KT-19827 formulation.

EXAMPLE D-3

Gandoerma wilt of coconut, which produces rhizomorph in the soil and girdles the tree at the collar by irrigating the base and roots of the tree, can be controlled with a 1 percent solution of KT-19827 (10 gallons per tree), and injecting one liter of a 1 percent solution in the trunk.

EXAMPLE D-4

Powdery mildew of cucurbits, caused by *Erysiphe chicoracearum, E. fuligena,* powdery mildew of apple (*Podosphaera leucotricha*), of grapes (uncinula necator), of various ornamentals including roses (*Sphaerotheca pannosa*) are controlled by spraying with a 1 percent solution of KT-19827.

EXAMPLE D-5

Downy mildew of grapes (*Plasmopara viticola*) causes whitish downy growth on the leaves and damping off and rotting of the leaves and fruits. The disease may be established in an experimental study by spraying a zoospore suspension of the fungus and incubating the inoculated plants in a humid chamber. For studying the protective effect of KT-19827, 10 plants bearing young leaves were sprayed with sporangial-zoospore suspension, and incubated in a moist chamber. Another 10 plants were previously sprayed with a 500 ppm solution of KT-19827, (0.05%) and 48 hours after, the plants were sprayed with the sporangian-zoospore suspension and incubated in the moist chamber. Ninety-six hours after, the plants were taken out and evaluated for disease scoring. None of the KT-19827 sprayed plants showed any disease symptoms, while the untreated ones showed yellowing and rotting of the leaves, and heavy growth of white sporangial mass of *Plasmopara viticola*.

Downy mildew of cucurbite (*Pseudo-peronospora cubensis*), of hops (*P. humuli*) and others are also controlled by spraying with 1 percent solution of KT-19827.

EXAMPLE D-6

Alternatia leaf spots of tomato and potato, *Cercospora arachidicola* and *C. personata* on peanuts, and numerous other leaf spots are well controlled by 1 percent spray of KT-19827.

EXAMPLE D-7

Diseases of lawn, particularly winter killing patches, dollar spot of Kentucky blue grass caused by combined infection by Rhizoctonia-Pythium species and *Fusarium niyeale*, can be effectively controlled by watering the lawn with 500 to 1000 ppm solution of KT-19827 formulation. Not only is the disease controlled, but the whole lawn becomes very green as a uniform flush-green mat.

EXAMPLE D-8

Many other leaf spot diseases like coffee rust *Hemileia vastatrix,* apple scab fungus (*Venturia inaequalis*) and others are amenable for control by spraying with RT-19827 formulation.

EXAMPLE D-9

Seed treatment with the whole KT-19827 formulation without dilution, in the dosage range of 0.2 to 0.5 percent of the seed weight, controlled seed-borne infections of several species of Dreschslera on cereals tested, Septoria species on wheat, Phomopsis and *Cercospora kikuchii* on soybeans, *Cercospora beticola* on sugar beet seeds, Alternaria species on Brassica species, *Phoma lingam* on cabbage, etc., and other similar seedborne pathogenic dematiaceous fungi.

In addition, *Pseudomonas glycinea,* a bacterial disease of soybean seeds, and *Septoria glycinea,* a fungal disease of soybean seeds, are controlled by treating 2.5 lbs of soybean seeds with 20 cc of KT-19827 in commercial detergent, or in 10 (ten) cc of methanol (methyl alcohol). On planting the seeds, the germination was normal, and none of the seedlings showed symptoms of bacterial blight, or Phomopsis blight. There was no carry over of *Cercospora kikuchii* causing leaf disease nor Septoria blight. For comparison, Benlate (benzamidazole carbamate) fungicide of DuPont was used, which controlled the fungal diseases and not the bacterial blight.

At present, there are no bactericides available for controlling plant bacterial diseases. The previous use of streptomycin has been abandoned due to the development of resistant bacterial strains. Benlate (a benzimidezole carbamate of DuPont) controls the fungal diseases but not the bacterial diseases; KT-19827 offers the effective control of bacterial plant pathogens.

EXAMPLE D-10

Soil-borne Phytophthora species inciting great damage to important commercial crops like *P. fragariae* causing red stele of strawberry, *P. cinnamomea* on avocado roots, *Phytophtora megasperma* var. sojae on soybeans, *Phythium aphanidermatum* on papaya are controlled by irrigating the soil with a 500 ppm solution of the KT-19827 formulation in water. No phytotoxic effect of any kind is noticed in the treated plants.

EXAMPLE D-11

Bacterial blights of bean are incited by species of Xanthomonas. *Xanthomonas phaseoli, X. phaseolicola* and *Pseudomonas phaseolicola* are internally seed-borne. The pathogen is deep in the embryo. 15 cc of the KT-19827 formulation in commercial detergent, is added to 1 kilogram of the seed, thoroughly coating the seeds, and the seeds are planted after 12 hours. The fungicide-bactericide penetrates and decontaminates the seed from the pathogen. The seeds germinate normally without any phytotoxic symptoms, and are healthy.

To prevent field infection from neighboring plots, a foliar spray of KT-19827 at a concentration of 5 cc per liter (500 ppm active ingredient) protects the plant from foliar infection.

It is apparent that many modifications and variations of this invention as hereinbefore set forth may be made without departing from the spirit and scope thereof. The specific embodiments described are given by way of example only, and the invention is limited only by the terms of the appended claims.

The embodiments of the invention in which an exclusive property or privilege is claimed are defined as follows:

1. As a new chemotherapeutic agent, the tannate complex of picro cupric ammonium formate in aqueous solution wherein cupric ammonium formate is comprised of one mole of a water soluble cupric salt reacted with 2 to 2.9 moles of ammonium formate, and for each 100 parts by dry weight of cupric ammonium formate said complex includes from about 2 to 5 parts by weight of picric acid and about 0.5 to 3.5 parts by weight of tannic acid combined with about 2 to 10 parts by weight of surfactant sufficient to prevent separation of the tannate complex.

2. The complex of claim 1 wherein said surfactant is an alkali metal alkyl sulphate.

3. The complex of claim 2 wherein said surfactant is sodium lauryl sulphate.

4. The complex of claim 1 wherein the water soluble cupric salt is cupric sulphate.

5. The complex of claim 1 wherein the complex is admixed in amount from about 0.05 to about 50 percent with an agriculturally acceptable non-toxic carrier.

6. A process for the control of plant diseases caused by plant pathogenic fungi and bacteria which comprises treating diseased plants with an effective amount of a complex according to claim 5.

7. A process for the preparation of the complex of claim 1 which comprises reacting a water soluble cupric salt with from 1 to 1.45 stoichiometric equivalents of ammonium formate in aqueous medium, combining 100 parts by dry weight of the resulting cupric ammonium formate with about 0.5 to 3.5 parts by weight of tannic acid, adding about 2 to 5 parts by weight of picric acid and about 2 to 10 parts by weight of surfactant sufficient to prevent separation of the tannate complex.

8. A process according to claim 7 wherein picric acid is added in solution in a non-phosphate detergent or propylene glycol.

* * * * *

UNITED STATES PATENT AND TRADEMARK OFFICE
CERTIFICATE OF CORRECTION

PATENT NO. : 4,673,687
DATED : June 16, 1987
INVENTOR(S) : Mandayam J. Thirumalachar et al It is certified that error appears in the above-identified patent and that said Letters Patent is hereby corrected as shown below:

Column 11, line 59, "RT" should be --KT--.

Signed and Sealed this

Fifteenth Day of December, 1987

Attest:

DONALD J. QUIGG

Attesting Officer      Commissioner of Patents and Trademarks